US006027934A

United States Patent [19]
Powell

[11] Patent Number: 6,027,934
[45] Date of Patent: Feb. 22, 2000

[54] VACCINE FOR, DIAGNOSTIC ASSAY FOR AND METHOD OF TREATING PARASITIC HEMOFLAGELLATE PROTOZOA

[76] Inventor: Curtis Powell, 144-30 Sanford Ave., Apt. 6T, Flushing, N.Y. 11355

[21] Appl. No.: 08/737,078
[22] PCT Filed: Apr. 29, 1994
[86] PCT No.: PCT/US94/04706
§ 371 Date: Jan. 16, 1997
§ 102(e) Date: Jan. 16, 1997
[87] PCT Pub. No.: WO95/29699
PCT Pub. Date: Nov. 9, 1995
[51] Int. Cl.$^7$ ............................. C07H 21/02; C12N 15/00
[52] U.S. Cl. ........................................ 435/320.1; 536/23.1
[58] Field of Search .................................. 536/23.5, 23.1; 435/320.1

[56] References Cited

U.S. PATENT DOCUMENTS 4,298,590  11/1981  Bogoch .

FOREIGN PATENT DOCUMENTS 9222325  12/1992  WIPO .

OTHER PUBLICATIONS

Boehringer Mannheim Chemicals Catalog, see p. 557, 1991.
Kumar et al. PNAS 87:1337–1341, Feb. 1990.
Lazar et al. Mol. Cell. Biol. 8(3):1247–52, Mar. 1988.
Parsons, J.A. (ed) "Peptide Hormones", published by University Park Press, see Chapter 1, pp. 1–7 by Rudinger, Jun. 1976.
Burgess et al. J. Cell Biol. 111:2129–2137, Nov. 1990.
Infection and Immunity, "A Flagellar Pocket Membrane Fraction from *Tryponosoma Brucei rhodesinse*: Immunogold Localization and Nonvariant Immunoprotection" Olenick et al.; Jan. 1988, pp. 92–98.
Medical Journal of Zambia 10, 2, 3; Curtis Powell, "Identification of an Immunoprotective Subcelllular Fraction o *Trypanosoma, Brucei* and *T.Rhodesience*", 1976,pp. 32–34.
Medical Journal of Zambia 12, 3, 67; Curtis Powell, "Experimental Immunity Against Trypanosomiasis in Sheep", 1978, pp. 67–69.
"Experimental Immunity Against Trypanosomiasis", C. Powell; Jan. 1978, p. 1450.
Immunology Letters, 12; Ruiz et al.; "Immunoprotection of Mice Against *Trupanosoma Cruzi* with a Lyophilized Flagellar Fraction of the Parasite Plus Adjuvant", 1986, pp. 1–4.
Proc. Natl. Acad. Sci. USA; Coppens et al.; "Receptors for the Host Low Density Lipoprotiens on the Hemoflagellate *Trypanosoma Brucei*: Purification and Involvement in the Growth of the Parasite", Sep. 1988, pp. 6753–6757.
CRC Press, Inc.; E.T. Maggio; "Immunochemistry Techniques", 1987, pp. 167–179.
Journal of Biological Chemistry, vol. 267, No. 6, Feb. 25, 1992; J. Schatzle et al.; Molecular Cloning and Characterization of the Structural Gene Coding for the Developmentally Regulated Lysosomal Enzyme, α–mannosidase, in *Dictyostekuym Discoideum*:, pp. 4000–40007.
European Journal of Cell Biology, 49; 1989; "Endocytosis by African Trypanosomes. I. Three–dimensional Structure of the Endocytic Organelles in *Trypanosoma Brucei* and T. Congolense"; pp. 295–302.
European Journal of Cell Biology, 49; 1989; "Endocytosis by African Trypanosomes. II. Occurrence in Different Life–cycle Stages and Intracellular Sorting"; pp. 303–310.

*Primary Examiner*—Patricia A. Duffy
*Attorney, Agent, or Firm*—Norris, McLaughlin & Marcus, P.A.

[57] ABSTRACT

Nucleic acid and vectors encoding an immunodominant fragment of a unique protein antigen originally derived from *Trypanosoma brucei rhodesiense* organisms can be used to induce immunoprotection across the species of trypanosomes, all species of Leishmania, and other parasitic hemoflagellate protozoa. The fragment forms the basis of a vaccine, which is useful, in turn, to treat infections of parasitic hemoflagellate protozoa. The fragment also forms the basis of a set of diagnostic assays, which can be used to diagnose such parasitic hemoflagellate protozoa. Also disclosed are kits containing reagents needed to perform such diagnostic assays.

6 Claims, No Drawings

VACCINE FOR, DIAGNOSTIC ASSAY FOR AND METHOD OF TREATING PARASITIC HEMOFLAGELLATE PROTOZOA

BACKGROUND OF THE INVENTION

1. Field of the Invention

The present invention relates generally to the use of a novel vaccine to treat and novel assays to diagnose a host of hemoflagellate protozoal infections, including infections arising from a variety of African trypanosomes.

2. Description of the Related Art

The World Health Organization estimates that at least 37 million people are afflicted annually with a hemoflagellate protozoal infection, some fatally. As many, if not more, domestic protein producing animals are also similarly afflicted. A vaccine has not been produced prior to now because (1) the parasite's ability to change it's surface coat, in the case of African trypanosomes, (2) the ability to induce immunosuppression in all trypanosomes and Leishmania, and (3) the ability of the parasite to hide intracellularly at some point in the infection. Previously, in African trypanosomes, the only immunity that could be obtained was to a single isolate from a single strain. This immunity was ineffective against any other isolate from the same strain or any other strain or species of African trypanosomes.

Olenick et al., *Infect. Immun.*, 56: 92 (1988), report that a mixture of proteins of approximately 80, 74, 40 and 25 kDa, originally derived from the flagellar pocket of *Trypanosoma brucei rhodesiense* gives protection across variants of *Trypanosoma brucei rhodesiense*. However, it is unclear from Olenick et al. whether the antigens are common to all African trypanosomes or, indeed, to all hemoflagellate protozoa. In this regard, the mere fact that Olenick et al. achieved immunoprotection across variants of *Trypanosoma brucei rhodesiense* does not alone suggest that the antigens involved are common to other species of African trypanosomes or to other hemoflagellate protozoa.

Possibly, a similar protein gives immunoprotection across species of African trypanosomes. See, Powell, *Med. J. Zambia*, 10: 32 (1976); Powell et al., *Med. J. Zambia*, 12: 67 (1978); and Powell, *Experientia*, 34: 1450 (1978). Ruiz et al., *Immunol. Lett.*, 12: 1 (1986), report the flagellar antigens in *Trypanosoma cruzi* to be immunoprotective against *Trypanosoma cruzi*, but antibodies to this antigen also give antibodies to mammalian cardiac tissue (see U.S. Pat. No. 4,298,590). This flagellar pocket site on the parasite, in African trypanosomes, is also reported to be involved in receptor-mediated endocytosis. See, Coppens et al., *Proc. Natl. Acad. Sci. USA*, 85: 6753 (1988); Webster, *Eur. J. Cell Biol.*, 49: 295 (1989); and Webster et al., *Eur. J. Cell Biol.*, 49: 303 (1989).

Published patent application WO 92/22325 teaches that a unique protein antigen originally derived from *Trypanosoma brucei rhodesiense* organisms can be used to induce immunoprotection against all African trypanosomes, *Trypanosoma cruzi*, all species of Leishmania, and other parasitic hemoflagellate protozoa. However, sequence and other data that would facilitate the preparation of the antigen by recombinant means are not disclosed. Preparation by recombinant means is necessary to produce the vaccine in sufficient quantities to meet current needs and in a cost effective manner.

SUMMARY OF THE INVENTION

It was an object of the present invention to provide a vaccine generally useful to treat hemoflagellate protozoal infections.

It was another object of the present invention to provide a method for immunoprotection against hemoflagellate protozoal infections generally.

It was another object of the present invention to provide a means for diagnosing hemoflagellate protozoal infections in patients suffering therefrom.

It was a further object to provide such a vaccine and such methods relatively inexpensively.

These and other objects have now been met with the present invention wherein it has now been discovered that an immunodominant fragment of a previously described antigen derived from the flagellar pocket of *Trypanosoma brucei rhodesiense* gives immunoprotection across the genus of hemoflagellate protozoa. The nucleotide and amino acid sequence of the inventive immunodominant fragment have been discovered and are reported herein and are designated SEQ ID NO: 1.

One embodiment of the present invention, therefore, relates to isolated or synthetic DNA having a nucleotide sequence selected from the group consisting of:

(a) SEQ ID NO.: 1;

(b) a sequence complementary to (a);

(c) an immunoprotective fragment of (a) or (b);

(d) a sequence that hybridizes to (a), (b) or (c) under stringent conditions; and (e) degenerative variants of (a), (b), (c) or (d).

Another embodiment of the present invention relates to the protein encoded by the above-mentioned nucleotide sequence.

Another embodiment of the present invention relates to a recombinant cloning vehicle containing the above-mentioned nucleotide sequence in the proper orientation necessary to permit the expression of the protein encoded by the above-mentioned nucleotide sequence.

Another embodiment of the present invention relates to a vaccine for inducing immunity to infections caused by hemoflagellate protozoa comprising an effective amount therefor of a protein encoded by the above-mentioned nucleotide sequence and a pharmaceutically acceptable carrier.

Still another embodiment of the present invention relates to a method of inducing immunoprotection in a patient against parasitic hemoflagellate protozoal infections comprising vaccinating said patient with the above-mentioned vaccine.

Still another embodiment of the present invention involves a process for the detection of flagellar pocket antigens in a sample comprising:

(a) coating a solid substrate with antibodies to the above-mention protein;

(b) washing the coated substrate;

(c) contacting the washed coated substrate with a protein-containing solution;

(d) washing the substrate from step (c);

(e) incubating the substrate from step (d) with said sample;

(f) washing the substrate from step (e);

(g) adding radiolabeled or enzyme labeled antibody, said antibody being an antibody to the above-mentioned protein, to the substrate from step (f);

(h) incubating the substrate from step (g);

(i) washing the substrate from step (h); and either (j1) subjecting the substrate of step (i) to counting in a gamma counter; or (j2) subjecting the substrate of step (i) to ELISA and comparing the results of said ELISA to ELISA results from normal sera utilized as a control.

The invention also relates to a process for the detection of antibodies to flagellar pocket antigens in a sample comprising:

(a) adsorbing on a solid substrate, containing binding sites thereon, the above-mentioned protein;

(b) contacting the substrate from step (a) with a material to saturate the binding sites thereon;

(c) washing the substrate from step (b);

(d) contacting the substrate from step (c) with a sample to form a first resultant mass;

(e) incubating the resultant mass of step (d);

(f) washing the resultant mass of step (e);

(g) adding radiolabeled or enzyme labeled antibodies to human IgG or IgM to the resultant mass of step (f) to form a second resultant mass; and either (h1) subjecting the second resultant mass of step (g) to counting in a gamma counter; or (h2) subjecting the second resultant mass of step (g) to ELISA; and then (i) subjecting a normal sample utilized as a control to steps (a) through either (h1) or (h2); and (j) comparing the counts of either steps (h1) or (h2) and (i).

Another embodiment of the present invention relates to a process for the detection of flagellar pocket antigens in a sample comprising:

(a) contacting a first portion of a composition containing an antibody against the above-mentioned protein with a mixture of said sample and the above-mentioned protein in a labeled form, incubating and washing said first portion;

(b) contacting a second portion of said composition containing antibody with the same amount of said labelled protein in a control free of flagellar pocket antigens, incubating and washing said second portion;

(c) adding the same amount of a protein-containing composition to each of the compositions of steps (a) and (b) above, incubating both of said compositions, centrifuging each of said compositions and separating liquid from the solids therein;

(d) determining the extent of labelled protein in each of the resultant compositions from step (c) above; and (e) comparing the relative amount of labelled protein in each of the resultant compositions from step (c) to determine if the activity of the resultant composition containing the first portion is less than the activity for the resultant composition of the second portion, in which case the sample contains a flagellar pocket antigen.

A further embodiment of the present invention relates to a process for the detection of antibodies to flagellar pocket antigens in a sample comprising:

(a) contacting the sample with a solid substrate coated with the above-mentioned protein in a non-labelled form, incubating and washing said contacted sample;

(b) contacting the incubated washed product obtained from step (a) above with the above-mentioned protein in a labelled form, incubating and washing the resultant mass; and (c) determining the extent of labelled protein present in the resultant mass obtained by step (b) above.

The present invention also relates to a diagnostic test kit for detecting flagellar pocket antigens in a test sample comprising in one or more containers:

(a) a given amount of antibody to the above-mentioned protein, the antibody being bound to a solid support; and (b) a labelled antibody to the protein.

The present invention further relates to a diagnostic test kit for detecting the presence of antibodies to a flagellar pocket antigen comprising in one or more containers:

(a) a given amount of the above-mentioned protein, said protein being bound to a solid support; and either (b1) labelled antibodies to human IgG or IgM; or (b2) the above-mentioned protein in a labelled form.

ABBREVIATIONS AND DEFINITIONS

The following amino acids may be indicated by the following 3- or 1-letter codes elsewhere in the specification:

| Amino Acid | 3-Letter Code | 1-Letter Code |
| --- | --- | --- |
| Alanine | Ala | A |
| Arginine | Arg | R |
| Asparagine | Asn | N |
| Aspartic Acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The following terms, which appear elsewhere in the specification, are to be construed to have the indicated definitions:

The term "degenerate variants", as used herein, is meant to embrace all variants of a given nucleotide sequence, which, due to the degeneracy of the genetic code, encode the same amino acid sequence as the given nucleotide sequence.

The term "patient", as used herein, means humans and certain animals, especially, non-human mammals, particularly, other primates, camels, dogs, donkeys, camels, and domestic protein producing mammals such as cattle, sheep, goats and pigs.

The term "proper orientation", as used herein, means an orientation in a recombinant cloning vehicle which results in a reading frame which, when expressed, produces the desired protein.

The term "stringent conditions", as used herein, means conditions well known to those of ordinary skill in the art to be stringent enough to guarantee specificity yet flexible enough to allow formation of stable hybrids at an acceptable rate in the context of the particular hybridization protocol employed.

DETAILED DESCRIPTION OF THE INVENTION

The immunodominant fragment was originally prepared as described in the examples below.

The immunodominant fragment has been found to give immunoprotection across the genus of hemoflagellate protozoa. By way of example, the immunodominant fragment gives immunoprotection across the genus of African trypanosomes, e.g., *Trypanosoma brucei rhodesiense, Trypanosoma vivax, Trypanosoma congolense, Trypanosoma brucei gambiense, Trypanosoma evansi* or *Trypanosoma brucei brucei*. The immunodominant fragment also gives immunoprotection against *Trypanosoma cruzi* (an American sub-genus of Trypanosoma) and against species of Leishmania (a separate genus), e.g., *Leishmania mexicana, Leishmania brasilia, Leishmania major, Leishmania amazonenis, Leishmania donovani, Leishmania infantum* and *Leishmania chagasi* as well as all Old World Leishmaniasis and all New World Leishmaniasis.

The immunodominant fragment described herein may be incorporated into a vaccine, which is then useful for inducing immunoprotection against infections caused by hemoflagellate protozoa in susceptible hosts such as humans and certain animals, especially, non-human mammals, particularly, other primates, camels, dogs, donkeys, camels, and domestic protein producing mammals such as cattle, sheep, goats and pigs. For this purpose, the immunodominant fragment may be presented in association with any conventional pharmaceutically acceptable carrier.

The vaccine may also comprise an adjuvant for stimulating the immune response and thereby enhancing the effect of the vaccine. The convenient adjuvant for use in the present invention is, preferably, alum.

Conveniently, the vaccines are formulated to contain a final concentration of immunodominant fragment in the range of from about 100 μg to about 750 μg/ml, preferably about 500 μg/ml. After formulation, the vaccine may be incorporated into a sterile container which is then sealed and stored at low temperatures.

In order to induce immunity in humans and animals to infections caused by hemoflagellate protozoa, an effective amount of the vaccine, formulated as described above, is administered by subcutaneous, intradermal or intramuscular injection. While the preferred route would depend upon the particular vaccine, it is believed that intramuscular injection will be generally suitable. An effective amount of the vaccine is the amount which is sufficient to induce in the host human or animal an immunity to the infection. The effective amount will usually be achieved by three doses, each dose containing from 0.1 to 1.0 ml of the vaccine, depending upon the size of the human or animal followed in some cases by a booster at six months to one year after primary immunization. The subsequent doses or the booster will depend on the level of antibody in the blood as a result of the initial immunization, and in certain instances may be unnecessary.

In a particularly preferred embodiment, the immunodominant fragment is encoded by DNA having the nucleotide sequence of SEQ ID NO.: 1 and, therefore, the immunodominant fragment has the amino acid sequence of SEQ ID NO.:1.

Since a B-cell epitope typically comprises 5–8 amino acid residues, fragments of SEQ ID NO.: 1 that are immunoprotective are also contemplated and may be selected from the group consisting of the following fragments (numbers correspond to the numbering of the amino acid sequence depicted in SEQ ID NO: 1): 16–20, 17–21, 18–22, 19–23, 20–24, 21–25, 22–26, 23–27, 24–28, 25–29, 26–30, 27–31, 28–32, 29–33, 30–34, 31–35, 32–36, 33–37, 34–38, 35–39, 36–40, 37–41, 38–42, 39–43, 40–44, 41–45, 42–46, 43–47, 15–20, 16–21, 17–22, 18–23, 19–24, 20–25, 21–26, 22–27, 23–28, 24–29, 25–30, -continued 26–31, 27–32, 28–33, 29–34, 30–35, 31–36, 32–37, 33–38, 34–39, 35–40, 36–41, 37–42, 38–43, 39–44, 40–45, 41–46, 42–47, 14–20, 15–21, 16–22, 17–23, 18–24, 19–25, 20–26, 21–27, 22–28, 23–29, 24–30, 25–31, 26–32, 27–33, 28–34, 29–35, 30–36, 31–37, 32–38, 33–39, 34–40, 35–41, 36–42, 37–43, 38–44, 39–45, 40–46, 41–47, 13–20, 14–21, 15–22, 16–23, 17–24, 18–25, 19–26, 20–27, 21–28, 22–29, 23–30, 24–31, 25–32, 26–33, 27–34, 28–35, 29–36, 30–37, 31–38, 32–39, 33–40, 34–41, 35–42, 36–43, 37–44, 38–45, 39–46, 40–47, 12–20, 13–21, 14–22, 15–23, 16–24, 17–25, 18–26, 19–27, 20–28, 21–29, 22–30, 23–31, 24–32, 25–33, 26–34, 27–35, 28–36, 29–37, 30–38, 31–39, 32–40, 33–41, 34–42, 35–43, 36–44, 37–45, 38–46 and 39–47 and longer sequences within SEQ ID NO.: 1 that contain the foregoing fragments.

To produce large quantities of the immunodominant fragment, DNA encoding the amino acid sequence of the immunodominant fragment can be incorporated into and expressed in a suitable recombinant cloning vector according to conventional techniques. For details, see, for example, Sambrook et al., *Molecular Cloning: A Laboratory Manual,* Cold Spring Harbor Laboratory Press (1989). In a preferred embodiment, the recombinant cloning vector contains DNA encoding the amino acid sequence of SEQ ID NO.: 1.

The present invention is also directed to diagnostic tests for the direct detection of hemoflagellate protozoa flagellar pocket antigens and hemoflagellate protozoa flagellar pocket antibodies.

In order to detect such antigens and/or antibodies in the sera of infected humans or animals, radioimmunoassay (RIA) or enzyme-linked immunosorbent assay (ELISA) can be employed. Details concerning RIA and ELISA are well known and are not repeated here. Furthermore, fluorescence techniques can be employed in place of either RIA or ELISA. Again, such fluorescence techniques are well known to those skilled in the art and are not repeated here.

In those cases where a solid substrate is employed, then the solid substrate can be any conventional solid substrate, for example, polystyrene beads or the walls of a microtiter plate.

Washing, when necessary, is with any conventional solution, e.g., tris buffered saline.

When a protein-containing solution is required, it can also be any conventional solution, but is, preferably, bovine serum albumin (BSA) or gelatin.

Where counts are made with a gamma counter, then if the specimens have counts at least 2.1 times higher than counts of the control, then the specimens are considered to be positive.

The labeling of one of the reaction components can be brought about by the use of a reporter group, such as by incorporation of a radioactive atom or group, e.g., $I^{125}$, or by coupling the components to an enzyme, e.g., horseradish peroxidase, or a dyestuff, e.g., a chromophoric moiety or a fluorescent group.

The components concerned are preferably labelled by coupling to an enzyme, since the estimation of this is much simpler than, for example, the estimation of radioactivity, for which special apparatus is necessary.

The enzymes used are preferably those which can be colorimetrically, spectrophotometrically, or fluorimetrically determined. Non-limiting examples of enzymes for use in the present invention include enzymes from the group of oxidoreductases, such as catalase, peroxidase, glucose oxidase, beta-glucuronidase, beta-D-glucosidase, beta-D-galactosidase, urease, galactose oxidase and the like.

The coupling of the enzyme and the components can be brought about in a known way, for example, by the formation of an amide linkage by methods known from peptide chemistry.

The labelling with a radioactive isotope can also be performed in a known way. Isotopes useful for labeling are predominantly $I^{125}$, $I^{131}$, $C^{14}$ and $H^3$.

The incubation steps utilized in carrying out the above procedures can be effected in a known manner, such as by incubating at temperatures of between about 20° C. and about 50° C. for between about 1 hour and about 48 hours.

Washings as described above are typically effected using an aqueous solution such as one buffered at a pH of 6–8, preferably at a pH of about 8.0, employing an isotonic saline solution.

As described above, the present invention also concerns diagnostic test kits for conducting the above-described methods for detecting antigens and antibodies. Radiolabeled antibodies used in the above-described test kits can be packaged in solution form. Moreover, in the above-described test kits, enzyme or fluorescent labelled antibodies can be substituted for the described radiolabelled antibodies.

The invention will now be described in further detail with reference to the following non-limiting examples:

EXAMPLE 1

*Trypanosoma brucei rhodesiense* bloodstream forms are grown in rats until the rats are parasite full ($10^8$–$10^9$/ml). The rats are then sacrificed and the blood collected in PSG (phosphate buffered saline+15.0 gms of glucose/liter) in heparin coated tubes or citrate coated tubes. The blood is then placed on a DE-52 column (DEAE-52) and the parasites collected and spun down at 5000 rpm for 15 minutes. The parasites are freeze-thawed 3× and homogenized and then centrifuged for 15 minutes at 1,500 rpm for 15 minutes. The precipitate is re-homogenized and re-centrifuged 3× in PBS (phosphate buffered saline) buffer. The homogenates are pooled and centrifuged for 20 minutes at 5,400 rpm. The precipitate is then mixed with renografin-60 and placed at the bottom of a centrifuge tube followed by a 20–40% renografin-0.25 M sucrose gradient and centrifuged for 2 hours at 18,000 rpm in a swinging bucket rotor. The second band is isolated and placed on a column of Sepharose 4B and eluted with chloroform.

This is mixed with ovalalbumin (1:1) and then with alum (1:1.5) and injected into the footpads of rats/mice every fortnight 3×. The antibodies are taken from behind the eye and centrifuged for 15 minutes at 12,000 rpm.

EXAMPLE 2

A lambda zap II (Stratagene, La Jolla, Calif.) cDNA expression library of *Trypanosoma brucei rhodesiense* was expressed on Bluescript *E. coli* (Stratagene, La Jolla, Calif.) on agar plates. The resultant plaques were treated with antibodies from the above (antibodies to the immunoprotective antigen from the flagellar pocket of *Trypanosoma brucei rhodesiense*). The antibodies reacted positively with 0.02% of these plaques. These positive plaques were isolated and transformed into phagemids using helper phage A408 (Stratagene, La Jolla, Calif.). These phagemids were transformed into Bluescript *E. coli* and induced with isopropyl-B-D-thiogalactopyranoside (IPTG-1.0 mg/ml). These expression products were lysed with lysozyme and pelleted. The pellet with the immunoprotective activity was resuspended in PBS.

EXAMPLE 3

60 cattle (zebu) were used. These cattle were divided into three groups of twenty cattle each. The first group were inoculated with the antigen described in WO 92/22325 (a), the second group with the inventive immunodominant fragment (b), and the third group was left untreated (c). The cattle were then challenged with trypanosomes (*T. vivax* and *T. congolense*) obtained from tsetse flies from Lambwe valley, Kenya. Group (a) had 4/20 infections, group (b) had 3/20 infections and group (c) had 13/20 infections. The infections from (a) and (b) were caused by too early treatment as these infections seemed to be disappearing. The animals were utilized in two sections. The first section was challenged for three weeks and had (a) 4/10 and (b) 3/10 and (c) 7/10 infections. The second section was challenged for four weeks and had (a) 0/10 and (b) 0/10 and (c) 6/10 infections.

EXAMPLE 4

36 C57BL/6 mice were used for Experiment 1, 40 for Experiment 2, and 76 for Experiment 3. These mice were divided into four groups of 30 (5 for Experiment 1, 10 for Experiment 2 and 15 for Experiment 3 or "5-10-15"), 42 (11-10-21), 40 (10-10-20) and 40 (10-10-20). The first group were untreated and served as controls, the second group were treated with the uncloned vector protein (Bluescript *E. coli* lysed in the same fashion as the cloned immunodominant fragment), the third group were treated with the antigen described in WO 92/22325 and the fourth group were treated with the cloned immunodominant fragment. The results are tabulated below:

| | Experiment 1 | | |
|---|---|---|---|
| Antigen | Infected | Uninfected | P |
| Untreated Controls** | 5/5 | 0/5 | |
| Bluescript Vector Lysed Pellet** | 9/11 | 2/11 | |
| WO 92/22325 | 6/10 | 4/10 | (N.S.)* |
| Immunodominant Fragment | 1/10 | 9/10 | <0.05 |

\* = Not Significant  
\*\* = Combined for the determination of P

| | Experiment 2 | | |
|---|---|---|---|
| Antigen | Infected | Uninfected | P |
| Untreated Controls** | 10/10 | 0/10 | |
| Bluescript Vector Lysed Pellet** | 10/10 | 0/10 | |
| WO 92/22325 | 4/10 | 6/10 | <0.80 |
| Immunodominant Fragment | 4/10 | 6/10 | <0.80 |

\*\* = Combined for the determination of P

| | Experiment 3 | | |
|---|---|---|---|
| Antigen | Infected | Uninfected | P |
| Untreated Controls** | 15/15 | 0/15 | |
| Bluescript Vector Lysed Pellet** | 19/21 | 2/21 | |

-continued

| Experiment 3 | | | |
|---|---|---|---|
| Antigen | Infected | Uninfected | P |
| WO 92/22325 | 10/20 | 10/20 | <0.001 |
| Immunodominant Fragment | 5/20 | 15/20 | <0.001 |

** = Combined for the determination of P

Collectively, the data from Examples 3 and 4 demonstrate that the antigen from WO 92/22325 was immunoprotective (infectivity in cattle was reduced from 13/20 to 4/20 and infectivity in mice was reduced from 68/72 to 20/40). Surprisingly, the immunodominant fragment according to the present invention gave even better protection than the antigen from WO 92/22325 (infectivity in cattle was reduced further to 3/20 and infectivity in mice was halved, i.e., reduced to 10/20).

It will be appreciated that the instant specification and claims are set forth by way of illustration and not limitation, and that various modifications and changes may be made without departing from the spirit and scope of the present invention.

What is claimed is:

1. An isolated or synthetic DNA sequence consisting of a nucleotide sequence that encodes the protein of SEQ ID NO: 2.

2. Isolated or synthetic DNA according to claim 1 consisting of SEQ ID NO: 1.

3. A recombinant vector wherein the inserted DNA is the isolated or synthetic DNA according to claim 1.

4. A recombinant vector according to claim 3, wherein the inserted DNA is SEQ ID NO 1.

5. An isolated or synthetic DNA sequence consisting of a nucleotide sequence encoding a fragment of the protein of SEQ ID NO: 2, which fragment, when administered to a patient, confers on said patient immunoprotection against infection of a parasitic hemoflagellate protozoa.

6. A recombinant vector wherein the inserted DNA is the isolated or synthetic DNA according to claim 5.

* * * * *

```
                          SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
        (A) LENGTH: 141 nucleotides
        (B) TYPE: nucleic acid
        (C) STRANDEDNESS: double
        (D) TOPOLOGY: linear (xi) SEQUENCE DESCRIPTION:  SEQ ID NO: 1:

TTT TTT TTT TTT TTT TTT TTT TTT TTT TTT TTT TTT                    36
Phe Phe Phe Phe Phe Phe Phe Phe Phe Phe Phe Phe
 1               5                  10

TTT TTT TTT TTT TTT TTT TTT TTT ATT ATT ATC CCC                    72
Phe Phe Phe Phe Phe Phe Phe Phe Ile Ile Ile Pro
            15                  20

TTT CAT TCC TCC CTA CTA ACA CGT GTT GTT TTG CGT                   108
Phe His Ser Ser Leu Leu Thr Arg Val Val Leu Arg
25                  30                  35

AGC TAC GCT CAT AGC AAA AAA AAA AAA AAA AAC                       141
Ser Tyr Ala His Ser Lys Lys Lys Lys Lys Asn
                40                  45

(2) INFORMATION FOR SEQ ID NO: 2:

(i) SEQUENCE CHARACTERISTICS:
        (A) LENGTH: 47 amino acids
        (B) TYPE: amino acid
        (D) TOPOLOGY: linear (xi) SEQUENCE DESCRIPTION:  SEQ ID NO: 2:

Phe Phe Phe Phe Phe Phe Phe Phe Phe Phe Phe Phe
 1               5                  10

Phe Phe Phe Phe Phe Phe Phe Phe Ile Ile Ile Pro
            15                  20

Phe His Ser Ser Leu Leu Thr Arg Val Val Leu Arg
25                  30                  35

Ser Tyr Ala His Ser Lys Lys Lys Lys Lys Asn
                40                  45
```